US005965128A

United States Patent [19]
Doyle et al.

[11] Patent Number: 5,965,128
[45] Date of Patent: Oct. 12, 1999

[54] **CONTROL OF ENTEROHEMORRHAGIC *E. COLI* 0157:H7 IN CATTLE BY PROBIOTIC BACTERIA AND SPECIFIC STRAINS OF *E. COLI***

[75] Inventors: Michael P. Doyle; Tong Zhao, both of Peachtree City; Barry G. Harmon, Athens; Cathy Ann Brown, Bogart, all of Ga.

[73] Assignee: University of Georgia Research Foundation Inc., Athens, Ga.

[21] Appl. No.: 08/910,850

[22] Filed: Aug. 13, 1997

[51] Int. Cl.⁶ .............................. A01N 63/00; C12N 1/20
[52] U.S. Cl. ..................... 424/93.48; 435/252.8; 435/849
[58] Field of Search ..................... 424/93.48; 435/252.8, 435/849

[56] References Cited

U.S. PATENT DOCUMENTS

| | | | |
|---|---|---|---|
| 3,956,482 | 5/1976 | Hahn et al. | 424/93 |
| 4,138,498 | 2/1979 | Das | 426/2 |
| 4,335,107 | 6/1982 | Snoeyenbos et al. | 424/93 |
| 4,689,226 | 8/1987 | Nurmi et al. | 424/93 |
| 4,794,080 | 12/1988 | Mays et al. | 435/42 |
| 5,302,388 | 4/1994 | Doyle et al. | 424/93 C |
| 5,308,615 | 5/1994 | De Loach et al. | 424/93 C |
| 5,340,577 | 8/1994 | Nisbet et al. | 424/93.21 |
| 5,478,557 | 12/1995 | Nisbet et al. | 424/93.21 |
| 5,549,895 | 8/1996 | Lyon et al. | 424/115 |
| 5,589,168 | 12/1996 | Allen et al. | 424/93.4 |

FOREIGN PATENT DOCUMENTS

| | | | |
|---|---|---|---|
| 95/16461 | 6/1995 | WIPO | A61K 39/02 |
| 96/00233 | 1/1996 | WIPO | C07H 21/04 |

OTHER PUBLICATIONS

Bell, P.B. et al. (1994) "A Multistate Outbreak of *Escherichia coli* O157–H7–Associated Bloody Diarrhea and Hemolytic Uremic Syndrome From Hamburgers" *JAMA.* 272:1349–1353.

Bradley, D.E. et al. (1991) "Colicinogeny of O157:H7 enterohemorrhagic *Escherichia coli* and the shielding of colicin and phage receptors by their O–antigenic side chains" *Can. J. Microbiol.* 37:97–104.

Brown, C. et al. (1995) "Experimental *E. coli* O157:H7 Infection In Calves" *Vet. Pathol.* 32:587.

Cray, C.W. et al. (1995) "Experimental infection of calves and adult cattle with *Escherichia coli* O157:H7" *Appl. Environ. Microbiol.* 61:1585–1590.

Griffin, P.M. et al. (1991) "The epidemiology of infections caused by *Escherichia coli* O157:H7, Other enterohemorrhagic *E. coli*, and the associated hemolytic uremic syndrome" *Epidemiol. Rev.* 13:60–98.

Hinton, Spates et al. Jul., 1991 "In vitro inhibition of the growth of *Salmonella typhimurium* and *Escherichia coli* O157:H7 by bacteria isolated from the cecal contents of adult chickens" *J. Food Protection.* 54(7):496–501.

Meng, J. et al. Jul., 1996. "Competitive Exclusion as a Method to Prevent Colonization of *E. coli* 0157:H7 In Cattle." Society for Industrial Microbiology Annual Meeting.

Murinda, S.E. et al. (1996) "Evaluation of Colicins for Inhibitory Activity against Diarrheagenic *Escherichia coli* Stains, Including Serotype O157:H7" *Appl. Environ. Microbiol.* 62:3196–3202.

Padhye, N.Y. et al. (1992) "*Escherichia coli* O157:H7 Epidemiology, pathogenesis and methods for detection in food" *J. Food. Prot.* 55(7):555–565.

Rasmussen et al. (1993) "Rumen contents as a reservoir of enterohemorrhagic *Escherichia coli*" *FEMS Microbiol. Lett.* 114:79–84.

Wang, G. et al. (1996) "Fate of enterohemorrhagic *Escherichia coli* O157:H7 in bovine feces" *Appl. Environ. Microbiol.* 62:2567–2570.

Zhao, T. et al. (1995) "Prevalence of Enterohemorrhgic *Escherichia coli* O157:H7 in a survery of dairy herds" *Appl. Environ. Microbiol.* 61(4):1290–1293.

Zhao, T. et al. Jun. 22–26, 1997 "Reduction of *Escherichia Coli* 0157:H7 In Dairy Cattle By Selected Probiotic Bacteria." VTEC 97. Shiga Toxin (Verotoxin)–Producing *Escherichia coli* Infections. Baltimore, MD.

Zhao, T. et al. Aug., 1995 "Development of a Species Specific Probiotic to Prevent/Reduce Carriage of *E. coli* 0157:H7 In Cattle." *Annual Report of the Center for Food Safety and Quality Enhancement.*

Zhao, S. et al. "Use of Vaccine and Biological Control Techniques to Control Pathogens in Animals Used for Food"; Sep. 1995, *Jounal of Food Safety*, 15:193–199.

Primary Examiner—Sandra E. Saucier
Assistant Examiner—Vera Afremova
Attorney, Agent, or Firm—Greenlee Winner and Sullivan PC

[57] ABSTRACT

The prevention and treatment of carriage of *E. coli* O157:H7 by a ruminant animal is accomplished by administering dominant probiotic bacteria to the animal. The dominant probiotic bacteria prevent the establishment of *E. coli* O157:H7 when inoculated prior to administering *E. coli* O157:H7, are reisolatable from the gastrointestinal tract of inoculated animals for up to 28 days post-inoculation, and are capable of reducing or eliminating *E. coli* O157:H7 from animals previously inoculated with the pathogen. In particular, the dominant probiotic bacteria are strains *E. coli* 271 ATCC 202020, *E. coli* 786 ATCC 202018 and *E. coli* 797 ATCC 202019.

13 Claims, 10 Drawing Sheets

1   2   3   4   5   6

CONTROL OF ENTEROHEMORRHAGIC *E. COLI* O157:H7 IN CATTLE BY PROBIOTIC BACTERIA AND SPECIFIC STRAINS OF *E. COLI*

STATEMENT REGARDING FEDERALLY SPONSORED RESEARCH AND DEVELOPMENT

Research underlying the invention was carried out in part with support of Grant No. 97-433 from the United States Department of Agriculture. The U.S. Government has certain rights in the invention.

BACKGROUND OF THE INVENTION

*E. coli* O157:H7, an important human pathogen causing hemorrhagic colitis and hemolytic uremic syndrome, has been reported with increased frequency during the past decade as a cause of human illness [for reviews, see Bell, P. B. et al. (1994) *JAMA* 272:1349–1353; Griffin, P. M. et al. (1991) *Epidemiol. Rev.* 13:60–98; Padhye, N. Y. et al. (1992) *J. Food Prot.* 55:555–565]. Cattle, especially young animals, have been implicated as a principal reservoir of *E. coli* O157:H7, with undercooked ground beef being a major vehicle of foodborne outbreaks. Also, the number of fruit-, fruit juice-, vegetable- (lettuce) and water- (including recreational lakes) related outbreaks have increased dramatically in recent years.

A recent national survey performed by the USDA National Animal Health Monitoring System revealed that 1.6% of feedlot cattle fecally shed *E. coli* O157:H7 and 0.4% shed *E. coli* O157:NM [Dagatz, D. (1995) USDA:APHIS:VS, Centers for epidemiology and animal health. Fort Collins, Colo. (personal communication)]. A major study of calves on dairy farms revealed that 1.5% that were between the age of weaning and 4 months shed *E. coli* O157:H7 in their feces [Zhao, T. et al. (1995) *Appl. Environ. Microbiol.* 61:1290–1293]. Experimental infection of calves and adult cattle with *E. coli* O157:H7 varies widely among animals of the same age group, but persists longer in calves than in adults and previous infection does not prevent reinfection by the same strain of *E. coli* O157:H7 [Cray, C. W. et al. (1995) *Appl. Environ. Microbiol.* 61:1585–1590]. Other animals, such as chickens, deer, and sheep have also been determined to have the ability to carry *E. coli* O157:H7 for an extended period of time.

Many public health concerns have been raised regarding *E. coli* O157:H7 contamination of foods. Such concerns have been heightened by the unique acid tolerance of *E. coli* O157:H7. Proper cooking is an effective method to kill *E. coli* O157:H7 in foods. However, unsanitary practices in preparing foods often result in foodborne illness, hence methods to reduce or eliminate carriage of *E. coli* O157:H7 in cattle are needed to reduce the public's exposure to the pathogen in food and the environment [Wang, G., et al. (1996) *Appl. Environ. Microbiol.* 62:2567–2570].

Vaccination has been the traditional approach to protecting cattle from carriage of harmful bacteria. However, *E. coli* O157:H7 does not adhere to or infect cattle. The primary sites of *E. coli* O157:H7 localization in calves are the rumen and colon. The rumen appears to be the most important site for long-term carriage of *E. coli* O157:H7, and may serve as the source of bacteria found in the colon [Brown, C., et al. (1995) *Vet. Pathol.* 32:587. Histologic examination of colon tissue revealed no evidence of attachment of *E. coli* O157:H7 to colon tissue. Hence, the presence of *E. coli* O157:H7 in the colon appears to be a transient state whereby the bacteria are passing through, rather than colonizing the colon. Vaccines are not likely to be effective in reducing the amount of *E. coli* O157:H7 carried and shed by cattle.

The amount of *E. coli* O157:H7 carried by calves can be affected by nutrition and management practices. Rasmussen, et al. [(1993) *FEMS Microbiol. Lett.* 114:79–841 determined that *E. coli* O157:H7 grew unrestricted in rumen fluid collected from fasted cattle.

Some strains of *E. coli* can produce colicins that are inhibitory in vitro, to diarrheagenic *E. coli* strains, including strains of serotype O157:H7 [Bradley, D. E., et al. (1991) *Can J. Microbiol.* 37:97–104; Murinda, S. E., et al. (1996) *Appl. Environ. Microbiol.* 62:3196–3202]. Murinda et al. assayed twenty-four *E. coli* colicin-producing strains and determined that all *E. coli* O157:H7 strains evaluated were sensitive to Col E1 to E8, K and N on mitomycin-C-containing agar and also to Col G, Col. H and MccB17 on Luria agar. Patterns of colicin-sensitivity and resistance have been used for strain identification. Biological control of a bacterial strain based on its bacteriocin-sensitivity has not been achieved. However, Doyle, et al. U.S. Pat. No. 5,302,388, disclosed prevention or inhibition of *Campylobacter jejuni* colonization of poultry by administering a selected bacterial strain capable of competing with *C. jejuni* for colonization sites in poultry cecum and of inhibiting growth of *C. jejuni*.

SUMMARY OF THE INVENTION

The present invention includes specific strains of probiotic *E. coli*, their isolation, characteristics and methods of use to prevent or treat *E. coli* O157:H7 carriage by a ruminant animal. By "probiotic" is meant bacteria having the property of preventing establishment of *E. coli* O157:H7 in a ruminant animal previously administered an effective dose of said probiotic bacteria. For example, calves first administered an effective amount of a strain of probiotic bacteria then subsequently administered *E. coli* O157:H7 do not become carriers of *E. coli* O157:H7 , while calves administered only *E. coli* O157:H7 continue to carry the strain for weeks, shedding the bacteria to the environment in feces. Of eighteen probiotic strains isolated in the present study, four were identified as "dominant" by which is meant that they could be reisolated from the gastrointestinal tract contents of inoculated animals at about 28 days post-inoculation.

Dominant probiotic bacteria were also shown to be capable of reducing or eliminating the *E. coli* O157:H7 from calves previously inoculated with *E. coli* O157:H7 and carrying the pathogen.

The invention therefore provides a method for preventing the carriage of *E. coli* O157:H7 by a ruminant by the step of administering an effective amount of a strain or combination of strains of probiotic bacteria to the ruminant prior to exposure to *E. coli* O157:H7. The method is especially useful for treating young ruminants, such as bovine calves, at an early age, before exposure to *E. coli* O157:H7 which may be present in the environment. The method is also useful to prevent animals shipped to a feedlot from being contaminated at the feedlot.

The invention further provides a method for reducing or eliminating *E. coli* O157:H7 from a ruminant by administering an effective amount of a strain or combination of strains of dominant probiotic bacteria. The method is useful to maintain cattle herds free of *E. coli* O157:H7 and to reduce carriage and fecal shedding of *E. coli* O157:H7 prior to slaughter.

The administration of probiotic bacteria is accomplished by feeding a feed supplement or additive which comprises an effective amount of probiotic bacteria, or by supplying a water treatment additive or inoculum to the animals' drinking water. The invention therefore provides a feed supplement composition comprising probiotic bacteria, and a water additive comprising probiotic bacteria.

The invention further includes a method for isolating probiotic bacteria which includes screening the growth supernatant of strains isolated from feces or intestine for ability to inhibit growth of *E. coli* O157:H7 on agar. A method for identifying dominant probiotic bacteria includes the step of inoculating a ruminant animal with a mixture of probiotic bacterial strains, then isolating the strains from the animal after a defined time period, for example, about 4 weeks. The reisolated strains are those which have successfully persisted in the animal, hence the term dominant probiotic bacteria. Reisolation and identification of dominant probiotic strains can be facilitated by the use of marker traits, either endogenous, selected or engineered, which allow each strain to be identified and/or selected from a mixture.

The methods for isolating probiotic bacteria, for isolating dominant probiotic bacteria, for preventing the carriage of *E. coli* O157:H7 and for treating an animal to reduce or eliminate *E. coli* O157:H7 from the animal are all applicable to other animals besides cattle, especially other ruminants, which have also been observed to carry *E. coli* O157:H7. At present, cattle are the most frequent carriers of *E. coli* O157:H7. The methods of isolation and use of dominant probiotic strains are accomplished by studies carried out with cattle. A large number of strains is available from natural sources which can meet the criteria of probiotic, and dominant probiotic bacteria. Repetitions of the herein-described isolation process may yield the same or different strains than those described herein. Such strains fall within the general categories of probiotic and dominant probiotic bacteria, as herein described.

DETAILED DESCRIPTION OF THE INVENTION

Figure 1:
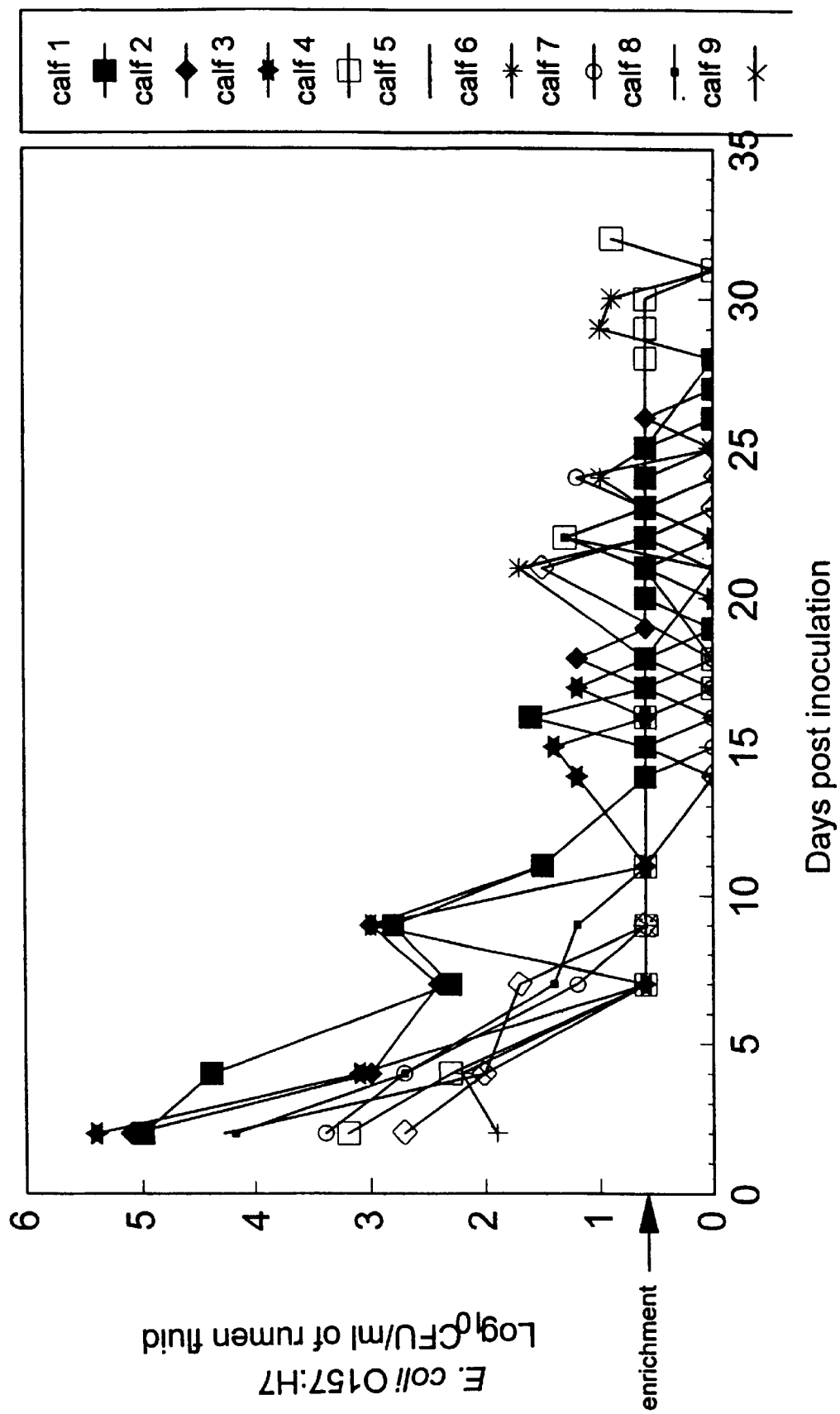
FIG. 1. is a graph showing the fate of *E. coli* O157:H7 in rumen fluid of calves administered only *E. coli* O157:H7. Arrow indicates detection of *E. coli* O157:H7 only be an enrichment procedure.

Histologic examination of colonic tissue has revealed no evidence of attachment of *E. coli* O157:H7 to bovine colonic tissue. The rumen appears to be the most important site for long-term carriage of *E. coli* O157:H7. The presence of O157:H7 bacteria in the colon is considered to be a transient state, the bacteria passing through from the rumen source and being shed in feces. Animals can be initially infected by ingestion of contaminated grass, feed or water. Results of the present study demonstrate that *E. coli* O157:H7 persists in the rumens of untreated calves up to 30 days after a single inoculant dose, and is shed in feces throughout the same time period. The O157:H7 bacteria are therefore carried by cattle along with any other microbial strains that inhabit the animals' digestive tract. For purposes of this invention, cattle and other animals in whose tissues or feces *E. coli* O157:H7 can be detected are said to carry *E. coli* O157:H7. The amount of *E. coli* O157:H7 carried by an animal is measurable in various ways, including sampling from various tissues. Most conveniently, the presence of *E. coli* O157:H7 can be measured in feces. Such measurement is of practical importance, since fecal contamination is the apparent source of meat contamination and also of reintroduction and infection of other animals. As shown herein, the amount of *E. coli* O157:H7 shed in feces is reflected in the amount measurable in the rumen. Therefore, the amount of *E. coli* O157:H7 in feces is a measure of the amount carried by the animal. Quantitative measurement of *E. coli* O157:H7 is expressed as colony forming units (CFU) per g feces or per ml rumen.

"Probiotic" is used herein as an adjective to describe bacteria isolated from a natural source and having the property of inhibiting the growth of *E. coli* O157:H7. The test of an inhibition used herein was an in vitro test on solid medium in which culture supernatants of candidate isolated bacteria were observed for their property of inhibiting *E. coli* O157:H7 growth when applied to the surface of the solid medium. Typically, a paper disc impregnated with the culture supernatant of a candidate strain was placed on the surface of an agar plate seeded with *E. coli* O157:H7. Probiotic bacterial supernatants caused a ring of clear agar or of reduced growth density indicating inhibition of *E. coli* O157:H7 in the vicinity of the disc. There are other tests for inhibition which are available or could be devised, including direct growth competition tests, in vitro or in vivo which can generate a panel of probiotic bacteria similar to that described herein. The bacterial strains identified by any such test are within the category of probiotic bacteria, as the term is used herein.

The term "dominant probiotic" is applied to probiotic bacteria which persist in, and are re-isolatable from an animal to which the bacteria have been administered. The criterion used in the work described herein was reisolation 26 days post-inoculation. Bovine calves were fed a mixture of 18 probiotic strains, then from a variety of tissues, digestive contents and feces were sampled 26 days post-inoculation. Four strains were recoverable, designated dominant probiotic strains. Other criteria can be employed, including shorter or longer time periods between inoculation and sampling. It is advisable to choose a time period sufficiently long that persistence of dominant probiotic strains can provide useful reduction of the amount of E. coli O157:H7 carried by the animal.

Isolation of dominant probiotic bacteria can be carried out by those of ordinary skill in the art, following the principles and procedures described herein. Of 1200 colonies isolated from cattle feces and tissues, 18 were probiotic and 4 were dominant probiotic. Therefore, the testing of similar numbers of independent isolates is reasonably likely to successfully yield dominant probiotic bacteria.

Administration of dominant probiotic bacteria can be accomplished by any method likely to introduce the organisms into the digestive tract. The bacteria can be mixed with a carrier and applied to liquid or solid feed or to drinking water. The carrier material should be non-toxic to the bacteria and the animal. Preferably, the carrier contains an ingredient that promotes viability of the bacteria during storage. The bacteria can also be formulated as an inoculant paste to be directly injected into an animal's mouth. The formulation can include added ingredients to improve palatability, improve shelf-life, impart nutritional benefits, and the like. If a reproducible and measured dose is desired, the bacteria can be administered by a rumen cannula, as described herein. The amount of dominant probiotic bacteria to be administered is governed by factors affecting efficacy. In the present study, $10^{10}$ CFU were administered in a single dose. Lower doses can be effective. When administered in feed or drinking water the dosage can be spread over a period of days or even weeks. The cumulative effect of lower doses administered over several days can be greater than a single dose of $10^{10}$ CFU. By monitoring the numbers of E. coli O157:H7 in feces before, during and after administration of dominant probiotic bacteria, those skilled in the art can readily ascertain the dosage level needed to reduce the amount of E. coli O157:H7 carried by the animals. One or more strains of dominant probiotic bacteria can be administered together. A combination of strains can be advantageous because individual animals may differ as to the strain which is most persistent in a given individual.

Dominant probiotic bacteria can be administered as a preventive, to prevent animals not presently carrying E. coli O157:H7 from acquiring the strain by exposure to other animals or environments where E. coli O157:H7 is present. Young calves and mature animals about to be transferred to a new location, such as a feed lot, are attractive candidates for preventive administration.

Treatment of animals carrying E. coli O157:H7 can be accomplished to reduce or eliminate the amount of E. coli O157:H7 carried by the animals, by administering dominant probiotic bacteria to E. coli O157:H7 infected animals. Animals known to be shedding E. coli O157:H7 in feces, or those raised where E. coli O157:H7 is known to exist are suitable candidates for treatment with dominant probiotic bacteria.

The methods for administering dominant probiotic bacteria are essentially the same, whether for prevention or treatment. Therefore, the need to first determine whether E. coli O157:H7 is being carried by the animals is removed. By routinely administering an effective dose to all the animals of a herd, the risk of contamination by E. coli O157:H7 can be substantially reduced or eliminated by a combination of prevention and treatment.

EXAMPLES

Example 1

Isolation of Probiotic Bacteria

Probiotic bacteria were isolated from cattle feces or cattle gastrointestinal tissue (intestine and colon). Fecal samples were collected from cattle that by fecal testing were confirmed negative for E. coli O157:H7. Fecal samples were serially diluted (1:10) in 0.1 M phosphate buffer, pH 7.2 (PBS) and 0.1 ml of each dilution was plated on Sorbitol MacConkey agar (SMA) plates. Plates were incubated for 16 h at 37° C. and up to ten colonies were randomly selected and each transferred to a test tube containing 10 ml of Trypticase soy broth (TSB) [(BBL, Becton Dickinson, Cockeysville, Md.).] Cultures were incubated for 16 h at 37° C. Tissue samples (1 g each) were homogenized (Ultra-Turrax T25 homogenizer, Janke & Kunkel IKA-labortechnik, Germany) at 9,500 rpm for 1 min and then 0.1 -ml portions were plated on the surface of SMA plates. Plates were incubated for 16 h at 37° C. Up to 10 colonies were each transferred to test tubes containing 10 ml TSB and incubated for 16 h at 37° C. The supernatant fluid from each culture was filter-sterilized (0.2 µm cellulose acetate membrane, Nalgene Co., Rochester, N.Y.).

Example 2

Screening Cultures for Anti-E. coli O157:H7 Properties

A 5-strain mixture of E. coli O157:H7, including 932 (human isolate), C7927 (human isolate), E009 (meat isolate), E0018 (cattle isolate), and E0122 (cattle isolate) was used to screen culture supernates for anti-E. coli O157:H7 metabolites. Approximately $10^7$ E. coli O157:H7 of approximately equal populations of each strain in 0.1 ml was surface-plated on duplicate SMA and TSA plates. A disc (12 mm in diameter) was placed on the surface of each SMA and TSA plate and 0.1 ml of filter-sterilized supernatant from a single culture was applied to the surface of the disc. In addition, a disc with 70% ethanol (positive control) and a disc with PBS (negative control) were applied to each plate. The cultures were incubated for 18 h at 37° C. and observed for zones of inhibition. A clear zone of more than 1 mm was considered as a positive response.

Example 3

Preparation of E. coli O157:H7 Cultures

The same 5-strain mixture described above was used. To facilitate enumeration of these bacterial isolates, the strains were induced for resistance to nalidixic acid (50 µg/ml). Each strain of nalidixic acid-resistant E. coli O157:H7 was transferred into 10 ml of tryptic soy broth (TSB) containing nalidixic acid (50 µg/ml) and incubated for 16–18 h at 37° C. with agitation (150 rpm). A 2-ml suspension of each isolate was transferred to 300 ml of TSB. After incubating at 37° C. for 16–18 h, the bacteria were sedimented by centrifugation (4,000×g for 20 min) and washed 3 times in PBS. PBS was added to sedimented bacteria in an amount needed to obtain an optical density (O.D.) of 0.5 at 630 nm ($10^8$ CFU/ml). A mixture of the 5 isolates ($2 \times 10^9$ CFU of each strain) of E. coli O157:H7 was mixed in 250 ml of 2% sterilized skim milk just prior to oral inoculation of calves. Bacterial populations were confirmed by enumeration on TSA and SMA containing nalidixic acid (50 µg/ml, SMA-NA) plates.

Example 4
Preparation of Probiotic Bacteria

All probiotic bacterial isolates were selected for nalidixic acid resistance (50 μg/ml) for ease of enumeration in feces. The bacteria were grown individually in 10 ml of TSB containing nalidixic acid (50 μg/ml). A 1-ml portion of each isolate was transferred to 100 ml of TSB. After incubating at 37° C. for 16–18 h, the bacteria were sedimented by centrifugation, washed, and adjusted to an O.D. at 630 nm of 0.5 using the method described above. The 18 strains of probiotic bacteria ($10^{10}$ CFU) were mixed in 250 ml of 2% sterilized skim milk just prior to oral inoculation of calves. The bacterial population was confirmed by enumeration of serial dilutions on TSA and SMA-NA plates in duplicate.

Example 5
Preparation of Calves

Fifteen single source male dairy calves were reared on milk replacer and weaned at 6 weeks of age prior to transfer to the University of Georgia. Calves were housed individually in climate-controlled BL-2 concrete rooms. Each room had an individual floor drain and was cleaned once daily. Calves were fed a mixture of alfalfa pellets and sweet feed twice daily and had free access to water. During a 2-week conditioning period, feces from all calves were sampled and tested negative, via fluorescent antibody staining, for bovine virus diarrhea, coronavirus, rotavirus, E. coli pilus antigens, and Cryptosporidia. Fecal floatation for intestinal parasites and bacterial culture for Salmonella and E. coli O157:H7 was performed and fecal pH was determined. After a 2-week preconditioning period, calves were surgically fitted with rumen cannulas (flexible rumen cannula). At least 10 days were allowed for surgical recovery and aftercare before the experiment begun.

Example 6
Rumen Cannulation

Feed was withheld from calves for 12 h. The left paralumbar fossa was clipped and scrubbed for standard surgical preparation. The fossa was anesthetized by using a paravertebral nerve block, inverted "L" block; Lidocaine, slightly smaller than the local anesthetic. A circular incision, slightly smaller than the diameter of the cannula, was made and the circular piece of skin and underlying cuticular and external abdominal oblique muscles were removed. Vessels were ligated as necessary and internal abdominal oblique, transverse muscles, and peritoneum were bluntly separated and retracted to create an opening to expose the rumen wall. The rumen wall was grasped with two large towel clamps for traction to exteriorize the rumen. The rumen wall was then sutured to the skin using #3 catgut or vetafil incorporating the muscle layers with a continuous suture pattern. The rumen wall was incised and a circular piece of rumen was removed and the cannula inserted. Calves were treated for 5 days after surgery with procaine penicillin G intramuscularly. The area between the cannula and the rumen wall was gently cleansed daily with betadine solution.

Example 7
Inoculation of Calves

Following a 12 h fast, calves were inoculated via rumen cannulation with 250 ml of skim milk containing probiotic bacteria. After 48 h, the 5-strain mixture of E. coli O157:H7 was inoculated via the same route. Control calves were challenged with the 5-strain mixture of E. coli O157:H7 only. Following challenge, calves were examined daily for clinical signs including depression, pyrexia, diarrhea, and anorexia. Rectal feces or samples collected from the fiscular tube were determined for pH, and enumeration of E. coli O157:H7 and probiotic bacteria.

Isolation and Enumeration of Bacterial Inocula: A sample of 10 g of feces or rumen content was collected through rectum retrieval or rumen cannulation daily after inoculating E. coli O157:H7. Samples were placed in a tube containing 15 ml of Cary-Blair transport medium, kept at 5° C., and transported to the Center for Food Safety and Quality Enhancement for analysis. A volume containing 1 g of feces was serially (1:10) diluted in 0.85% NaCl to $10^{-6}$ and 0.1 ml of each dilution was plated in duplicate on SMA-NA. Tissue samples of the entire gastrointestinal tract collected at necropsy were held at 5° C. until analysis. Content of each tissue from each segment was separated and weighed, and the tissue was rinsed with 100 ml of PBS. The rinsed tissue was added to 9 ml of PBS and homogenized for 1 min at 9,500 rpm with an Ultra-Turrax tissue homogenizer. A sample of 0.1 ml tissue or tissue content suspension was inoculated onto SMA-NA plates in quadruplicate and incubated at 37° C. for 24 h for enumeration of E. coli O157:H7 or probiotic bacteria. If these bacteria were not detected by the direct plating method, a selective enrichment method (17) (modified TSB containing 50 μg nalidixic acid/ml) was performed. Samples were each placed in 100 ml of selective enrichment medium and incubated at 37° C. for 24 h with agitation at 150 rpm. Dilutions of cultures were plated on SMA-NA and isolates were selected and further tested. Colonies typical of E. coli O157:H7 (sorbitol negative) were replated on SMA-NA and confirmed as E. coli by biochemical methods, and as O157 and H7 by serological methods. Probiotic bacteria were confirmed by DNA fingerprinting by pulsed-field gel electrophoresis (PFGE).

Example 8
Genomic Fingerprinting of Bacterial Isolates

Figure 9:
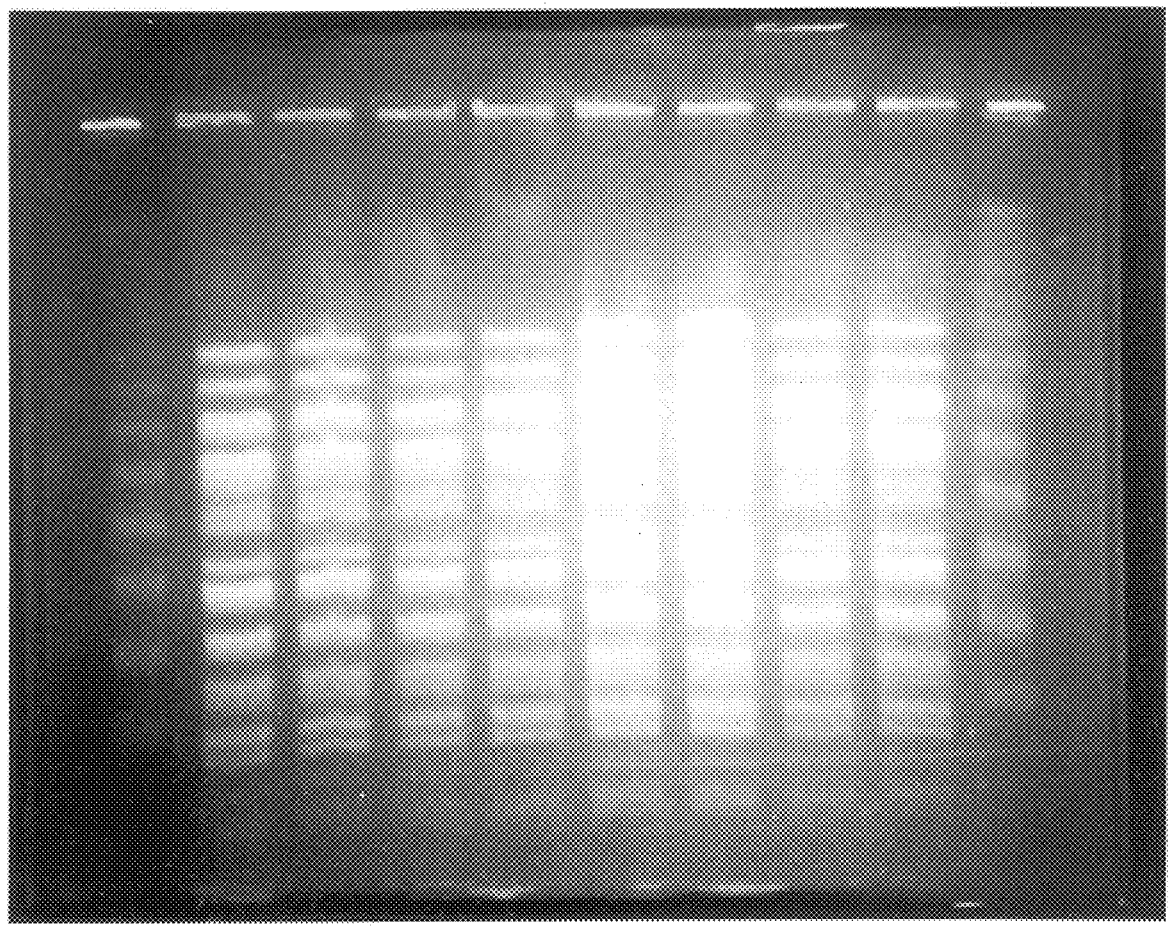
FIG. 9. profiles Xbal digests of genomic DNA of dominant probiotic bacteria by pulsed-field gel electrophoresis. Both left and right lane are λ ladders (48.5 kb). Lanes 1 to 8 are strain 271.
Figure 10:
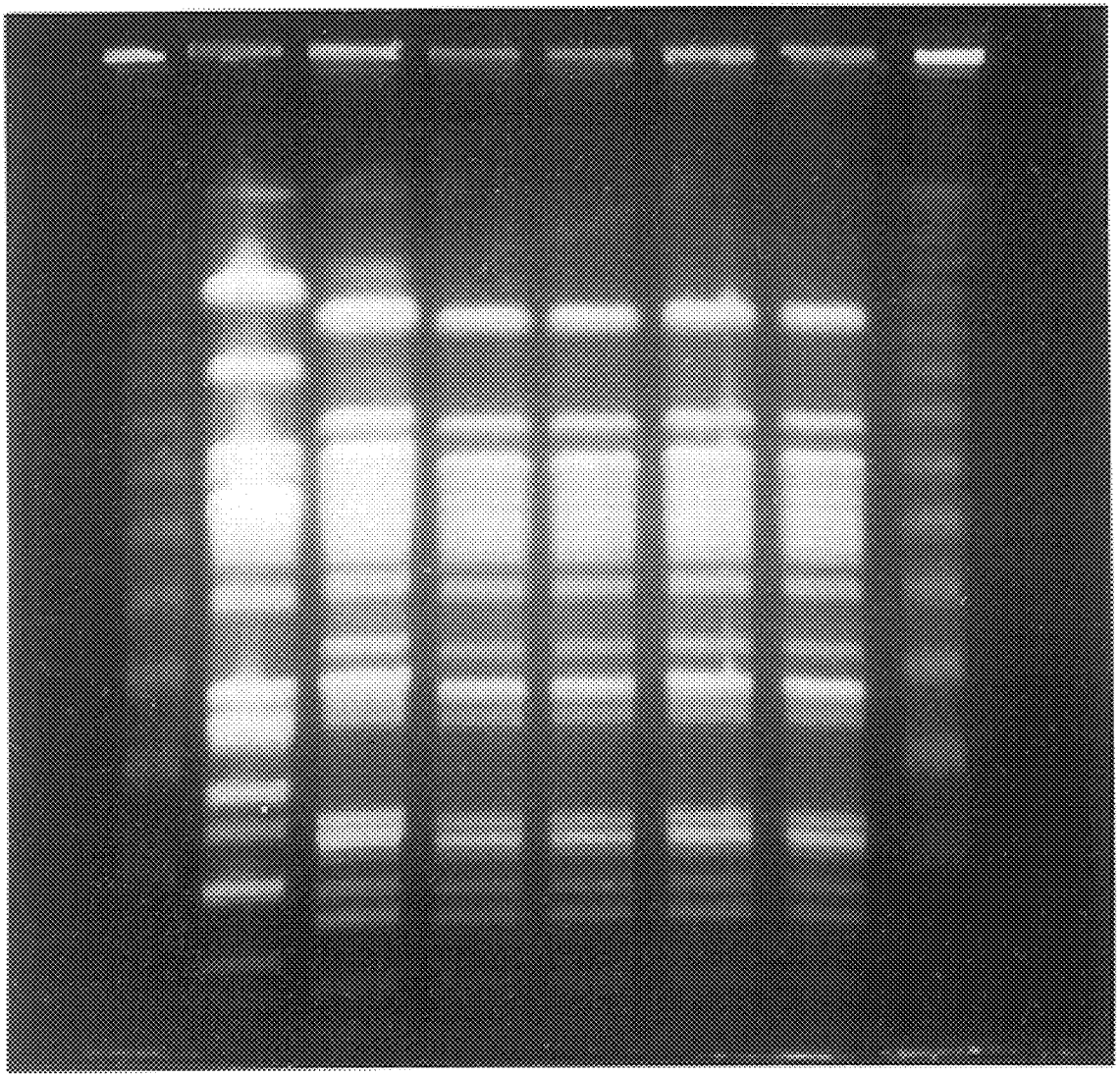
FIG. 10. profiles Xbal digests of genomic DNA of dominant probiotic bacteria by pulsed-field gel electrophoreses. Both left and right are λ ladders (48.5 kb). Lane 1 is strain 786, and lanes 2 to 6 are strain 797.

PFGE procedures similar to those described previously were used (14). Bacteria were grown in 10 ml of TSB at 37° C. for 24 h with agitation at 200 rpm. The bacteria were sedimented by centrifugation (4000×g, 20 min), washed three times in 75 mM NaCl containing 25 mM EDTA at pH 7.4 (SE), and resuspended in 0.5 ml of SE. The bacterial suspension was mixed with 0.5 ml of 2% (w/v) low melting point agarose in buffer consisting of 10 mM Tris, 10 mM $MgCl_2$, and 0.1 mM EDTA (TME), pH 7.5. This mixture was dispensed into sample molds and the agarose plugs were digested with proteinase K (2 mg proteinase K, 50 mM Tris, 50 mM EDTA, 1% N-Lauroylsacosine/ml, pH 8.0) at 56° C. overnight. The samples were washed in 10 mM Tris, 5 mM EDTA, pH 7.5 (TE), and digested with 50 U of XbaI. After incubating at 37° C. overnight, the reaction was stopped by the addition of 20 μl of 0.5 M EDTA. The DNA samples were electrophoresed on a 1.2% agarose gel in 0.5×TBE buffer by a contour-clamped homogeneous electric field device (CHEF MAPPER, BioRad). After electrophoresis for 24 h at 200 V with pulse times of 5–50 seconds and linear ramping and an electrical field angle of 120° at 14° C., the gels were stained with ethidium bromide and bands were visualized and photographed with UV transillumination. The results for 3 dominant probiotic strains, 271, 786 and 797 are shown in FIGS. 9 and 10.

Example 9
Necropsy of Calves

Calves were euthanatized with intravenous sodium pentobarbital. The gastrointestinal tract was clamped at the esophagus and rectum and removed in toto. Four to six-cm lengths of duodenum, proximal, middle, and distal jejunum, proximal and distal ileum, proximal and distal cecum, proximal loop of the ascending colon, centripetal turn and centrifugal turn of the spiral colon, transverse colon, and descending colon were double tied to allow sampling of all sections for enumeration of E. coli O157:H7 and probiotic bacteria in both the tissue and its content with minimal cross-contamination. Sections and contents of rumen, reticulum, omasum, and abomasum, and sections of kidney, spleen, liver, gall bladder, jejunal lymph node, ileal lymph node, cecal lymph node and tonsil also were collected for culture and enumeration of E. coli O157:H7 and/or probiotic bacteria. Sections from all of these sites, as well as sections of prescapular lymph node, skeletal muscle, skin, tonsil, thyroid, thymus, esophagus, heart, pancrease, umbilicus, adrenal, urinary bladder, and testes also were placed in 10% buffered formalin for histologic examination.

Example 10
Histopathology and Immunohistochemistry of Tissues

Fixed tissues were embedded in paraffin by standard methods, sectioned at 5 $\mu$m and stained with hematoxylin and eosin. Selected sections were Gram stained. The sections exhibiting large numbers of surface or luminal bacteria histologically were selected and treated by an alkaline phosphatase immuno-staining procedure to identify E. coli O157:H7. Tissues were deparaffinized in xylene for 10 min, rehydrated through graded alcohols, and rinsed in PBS. The sections were covered with E. coli O157:H7-specific antibody (Kirkegaard & Perry Laboratories, Inc., Gaithersburg, Md.) and incubated in a humidity chamber for 30 min at RT. After a 10-min rinse in PBS, slides were covered with a second antibody labeled with biotin for 20 min in a humidity chamber at room temperature (RT). The slides were rinsed for 10 min in PBS, returned to the humidity chamber, and the tissue sections were covered with alkaline phosphatase-conjugated streptavidin. After incubation at RT for 20 min, the slides were rinsed in PBS for 10 min, placed in the humidity chamber, and overlaid with substrate solution for 15 min. The slides were rinsed in PBS for 10 min, counterstained for 3 min with Mayer's hematoxylin, mounted with aqueous medium followed by nonaqueous mounting medium, and examined microscopically.

Example 11
Amounts of E. coli O157:H7 carried in absence and presence of probiotic bacteria In vitro screening of potential probiotic bacteria that secrete metabolite(s) inhibitory to E. coli O157:H7. Eighteen of 1,200 colonies isolated from cattle tissue and feces inhibited E. coli O157:H7 in vitro. Among them, five colonies were isolated from feces, five from the small intestine, and eight from the colon. Seventeen of the 18 colonies were identified as E. coli and the other as Proteus mirabilis. All were assayed for Shiga toxin production and none produced Shiga toxin. PFGE genomic DNA fingerprinting revealed 13 different profiles among the 18 isolates.

Colonization of calves by probiotic bacteria. One calf initially was fed one strain of probiotic bacteria (E. coli at $10^{10}$ CFU). The calf appeared to be normal, and this E. coli was recovered by the enrichment procedure from only the ileum and cecum at the termination of the experiment (12 days). Two calves then were fed the entire 18 strains (approximately equal concentrations, $5 \times 10^8$ CFU each) of probiotic bacteria ($10^{10}$ CFU/per calf) as a mixture. The calves feces were of normal consistency and the bacteria colonized the gastrointestinal tract for up to 27 days (at termination of the study counts were 50 to 200 CFU/g of feces).

Determination of dominant probiotic bacteria strains by PFGE. Twenty-one colonies isolated from the tonsil, omasum, reticulum, rumen, proximal ileum, distal cecum, proximal loop of ascending colon, transverse colon, and feces at 26 days postinoculation were analyzed by PFGE. Isolates with four DNA profiles were dominant and all were E. coli. Among the twenty-one colonies, nine were strain #797, seven were strain #786, three were strain #271, and two were strain #1019.

Pathological changes in calves by probiotic bacteria. Although some strains of the inoculated bacteria were recovered at necropsy from tissue specimens from different parts of the gastrointestinal tract, there were no pathological changes in any of the tissue samples assayed.

Figure 2:
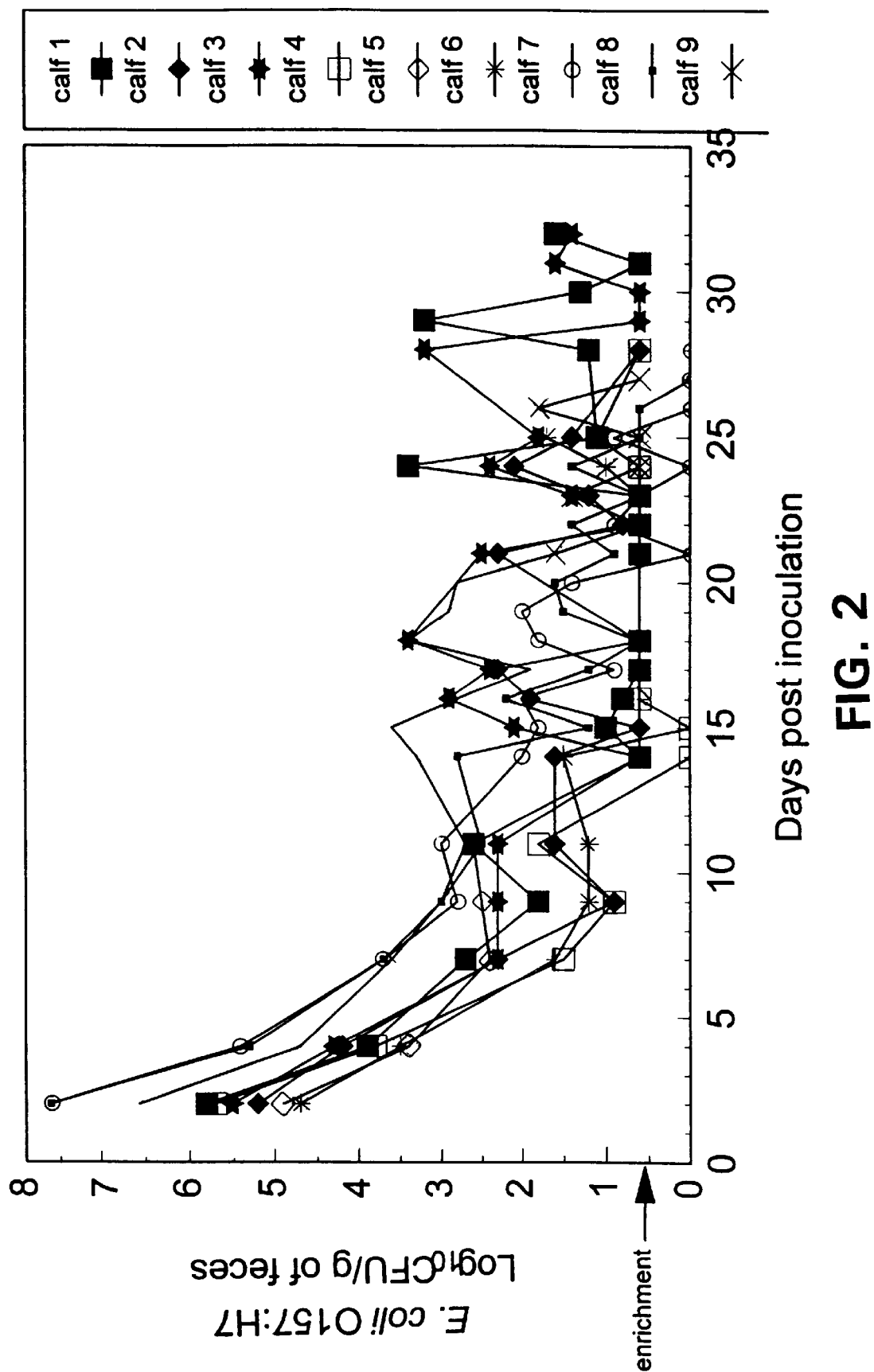
FIG. 2. is graph showing the fate of *E. coli* O157:H7 in feces of calves administered only *E. coli* O157:H7. Arrow indicates detection of *E. coli* O157:H7 only by an enrichment procedure.

Efficiency of probiotic bacteria in reducing carriage of E. coli O157:H7 in calves. Of the 9 calves administered only E. coli O157:H7, all remained healthy with no evidence of fever or diarrhea. E. coli O157:H7 was isolated intermittently from rumen fluid of all animals during 3 weeks post-inoculation (FIG. 1). Shedding of E. coli O157:H7 in feces at various levels was continuous throughout the experiment (mean 28 days) (FIG. 2). At necropsy, E. coli O157:H7 was isolated from rumen contents of eight of ten, and from the colon of 10 of 10 calves. No pathological changes were observed in any of the tissue samples examined.

Figure 3:
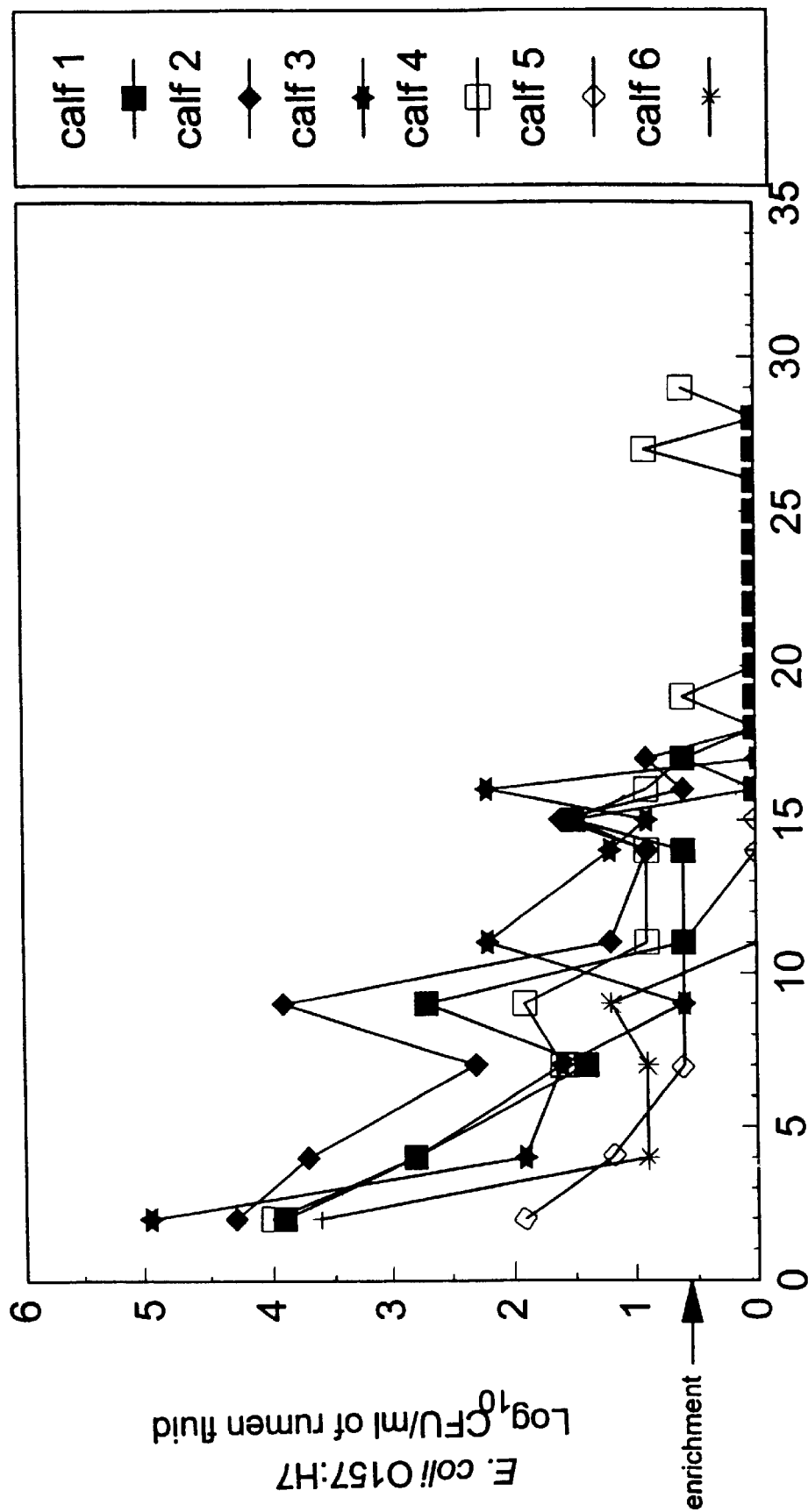
FIG. 3. is a graph showing the fate of *E. coli* O157:H7 in rumen fluid of calves administered probiotic bacteria and 2 days subsequently *E. coli* O157:H7. Arrow indicates detection of *E. coli* O157:H7 only by an enrichment procedure.
Figure 4:
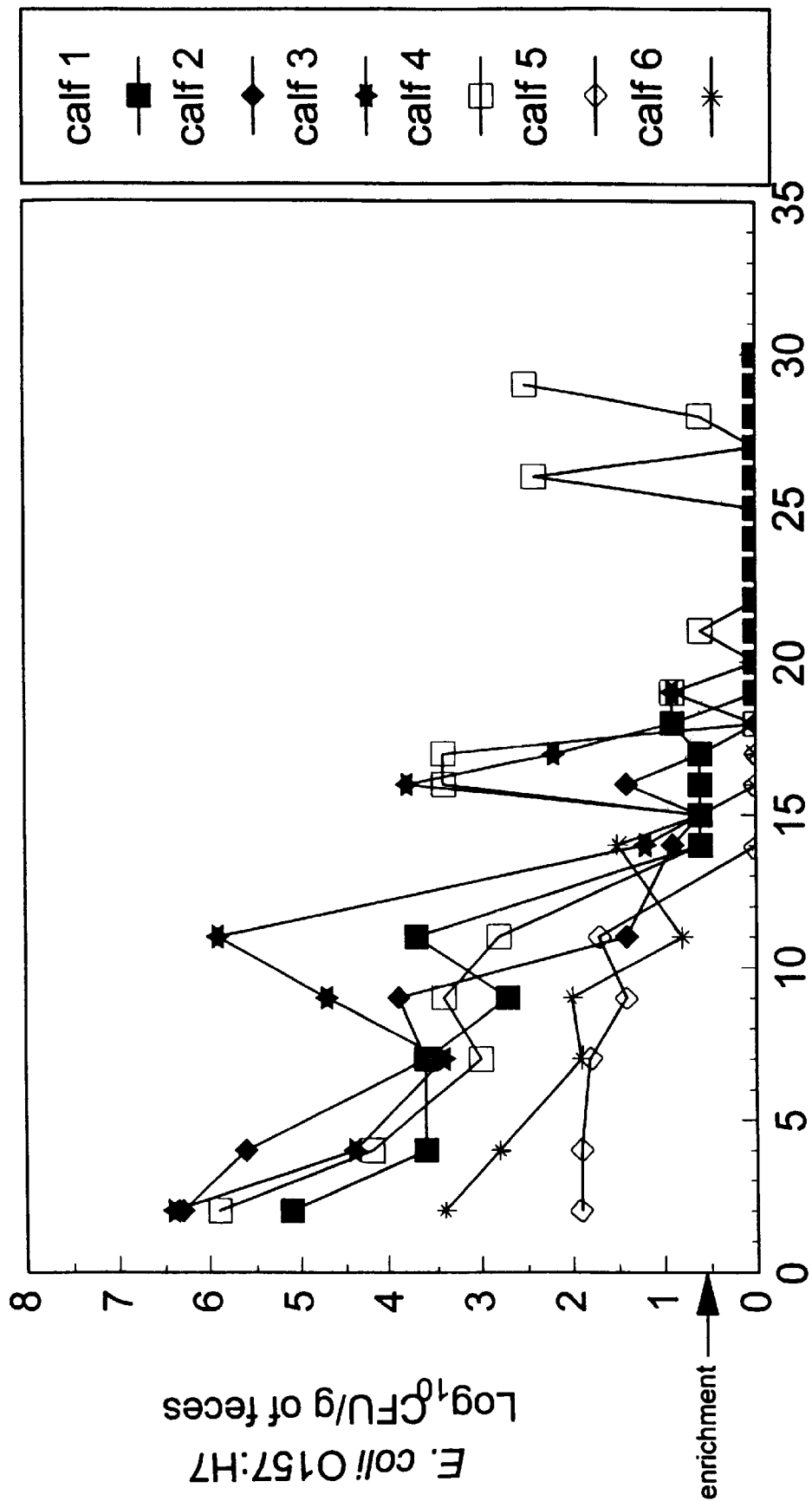
FIG. 4. is a graph showing the fate of *E. coli* O157:H7 in feces of calves administered probiotic bacteria and 2 days subsequently *E. coli* O157:H7. Arrow indicates detection of *E. coli* O157:H7 only by an enrichment procedure.

All calves that were administered probiotic bacteria 2 days before treatment with E. coli O157:H7 remained healthy with no evidence of fever or diarrhea. E. coli O157:H7 was detected in rumen samples collected through the fistula tube, for up to 9 days in two animals, 16 days in one animal, 17 days in two animals, and 29 days in one animal (FIG. 3). E. coli O157:H7 was detected in feces for up to 11, 15, 17, 18, 19, and 29 days (at termination of experiment) in each of one animal (FIG. 4). At necropsy (mean 30 days), E. coli O157:H7 was not recovered from rumen samples from any of these six animals; however, these bacteria were recovered from the colon of one of the six animals. The E. coli O157:H7-positive animal was twice fasted for 2-day periods (day 16, 17 and day 23, 24) postinoculation during the study. Four of the six probiotic-treated animals were fasted according to this protocol.

Example 12
Efficacy of Dominant Probiotic Bacteria as a Treatment for Reducing/Elimination E. coli O157:H7 in Cattle Preparation of Dominant Probiotic Bacteria. Four strains of E. coli (271, 797, 786 and 1019) previously determined to be inhibitory of E. coli O157:H7, were selected for nalidixic acid resistance (50 $\mu$g/ml) for ease of enumeration in feces. Approximately equal populations of each of the four strains were mixed (total $10^{10}$ CFU) into 50 ml of 2% sterilized skim milk for administration to calves. The E. coli populations were confirmed by enumeration on duplicate TSA and SMA-NA plates.

Inoculation of Calves. A total of 16 calves was used. Following a 24-h fast, each was administered a 5-strain mixture of E. coli O157:H7 in 50 ml of 2% sterilized skim milk ($10^{10}$ CFU) through a cannula tube. Two calves were treated with probiotic bacteria ($10^{10}$ CFU) through a cannula tube 1 day after administration of E. coli O157:H7. Two additional calves were treated with probiotic bacteria ($10^{10}$ CFU) 3 days after administration of E. coli O157:H7. Rumen samples collected through the cannula tube and rectal feces were enumerated daily for E. coli O157:H7 and probiotic bacteria.

Figure 5:
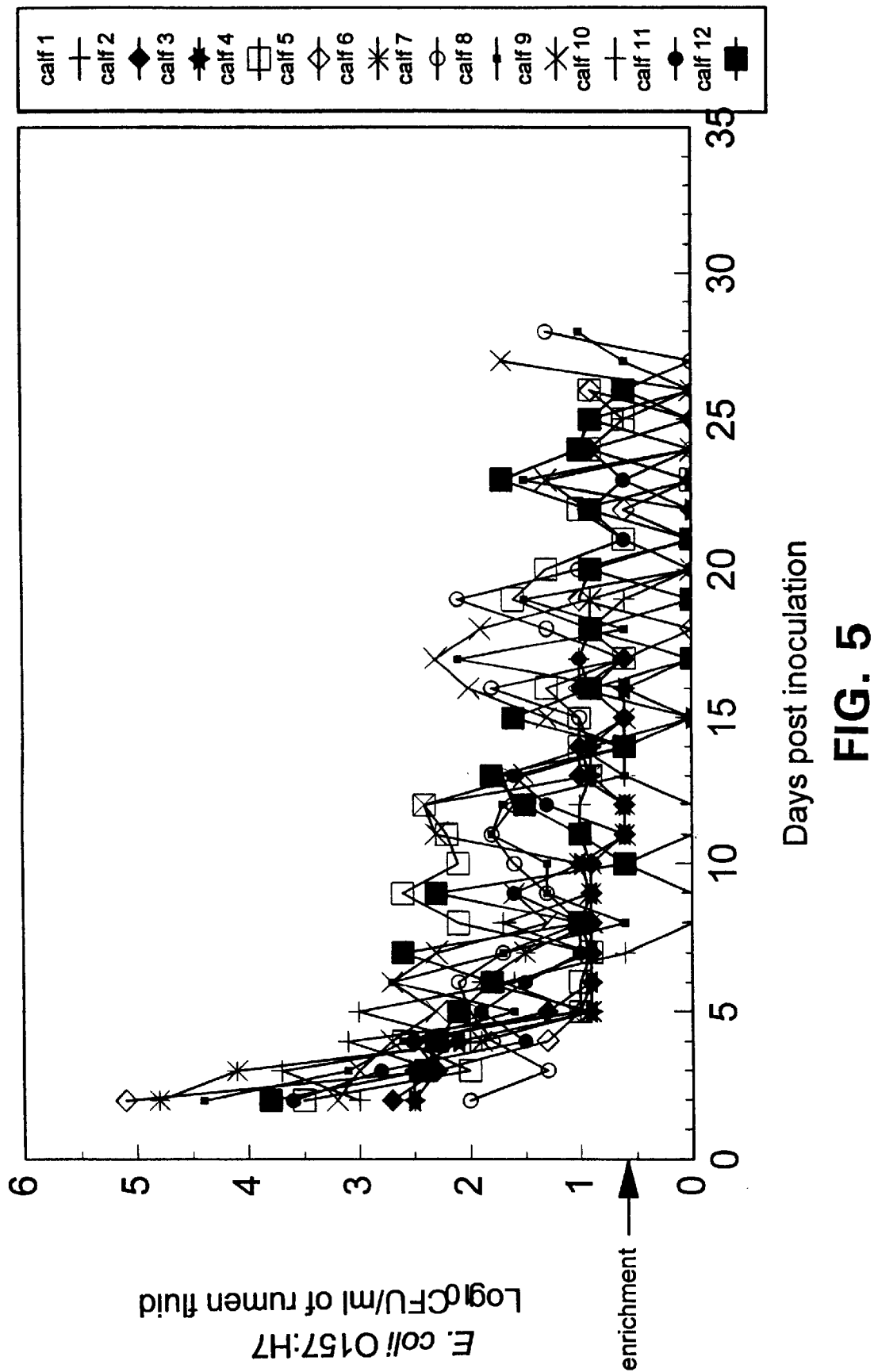
FIG. 5. is a graph of the fate of *E. coli* O157:H7 in rumen fluid of calves administered *E. coli* O157:H7 only. Arrow indicates detection of *E. coli* O157:H7 only by an enrichment procedure.
Figure 6:
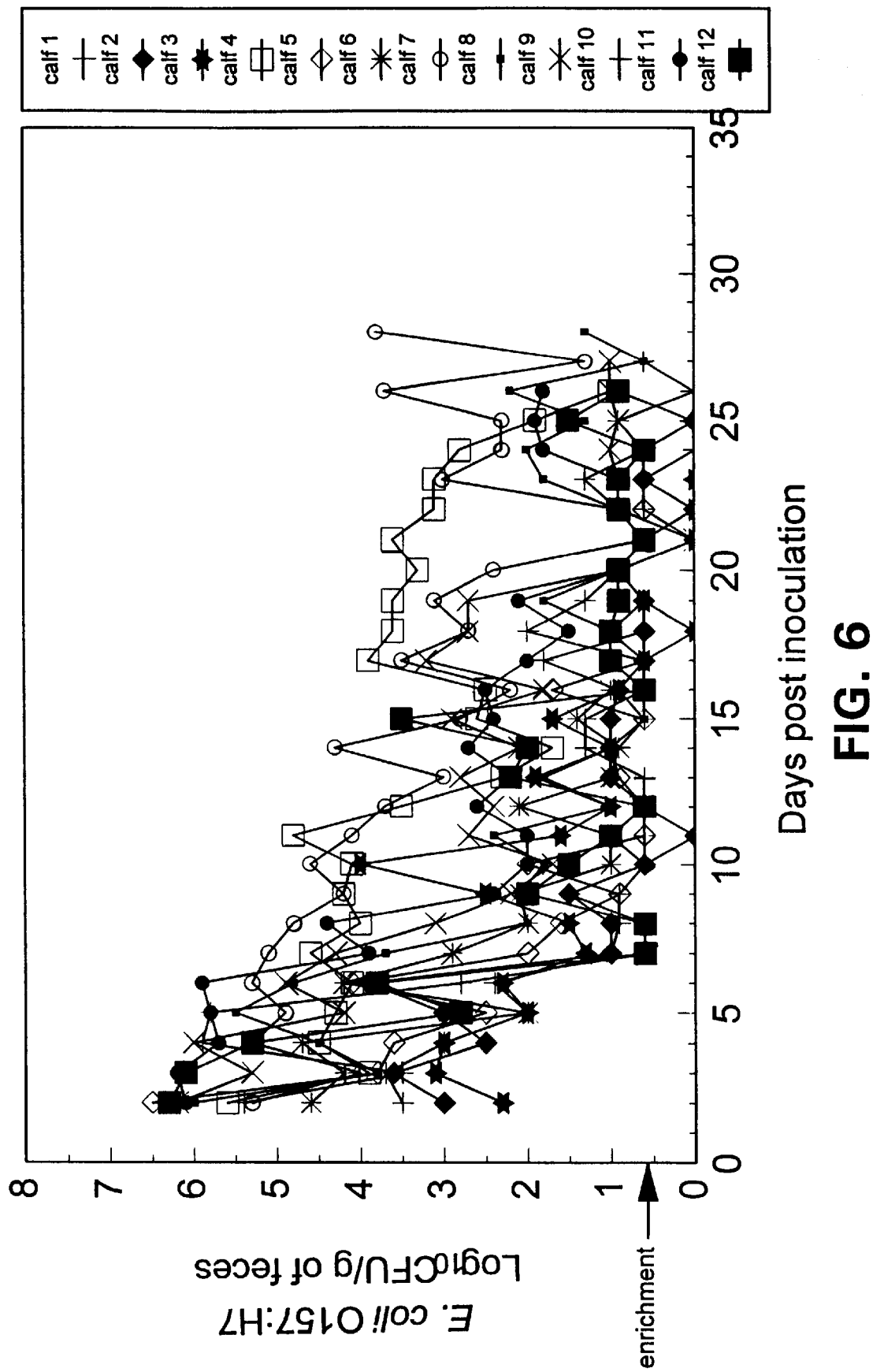
FIG. 6. is a graph of the fate of *E. coli* O157:H7 in feces of calves administered *E. coli* O157:H7 only. Arrow indicates detection of *E. coli* O157:H7 only by an enrichment procedure.

Efficiency of treatment of probiotic bacteria in reducing/eliminating carriage of E. coli O157:H7 in calves. Of the 12 calves administered only E. coli O157:H7 as positive controls, O157 was isolated intermittently from the rumen for up to 2 weeks from 1 animal, for 3 weeks from 3 animals, and for 4 weeks from 8 animals (FIG. 5). Continuous shedding of E. coli O157:H7 at various levels in the feces of 11 of 12 calves occurred throughout the study (FIG. 6). At necropsy E. coli O157:H7 was isolated from rumen contents of 9 of 12 calves and from the colon of 10 of 12 calves.

Figure 7:
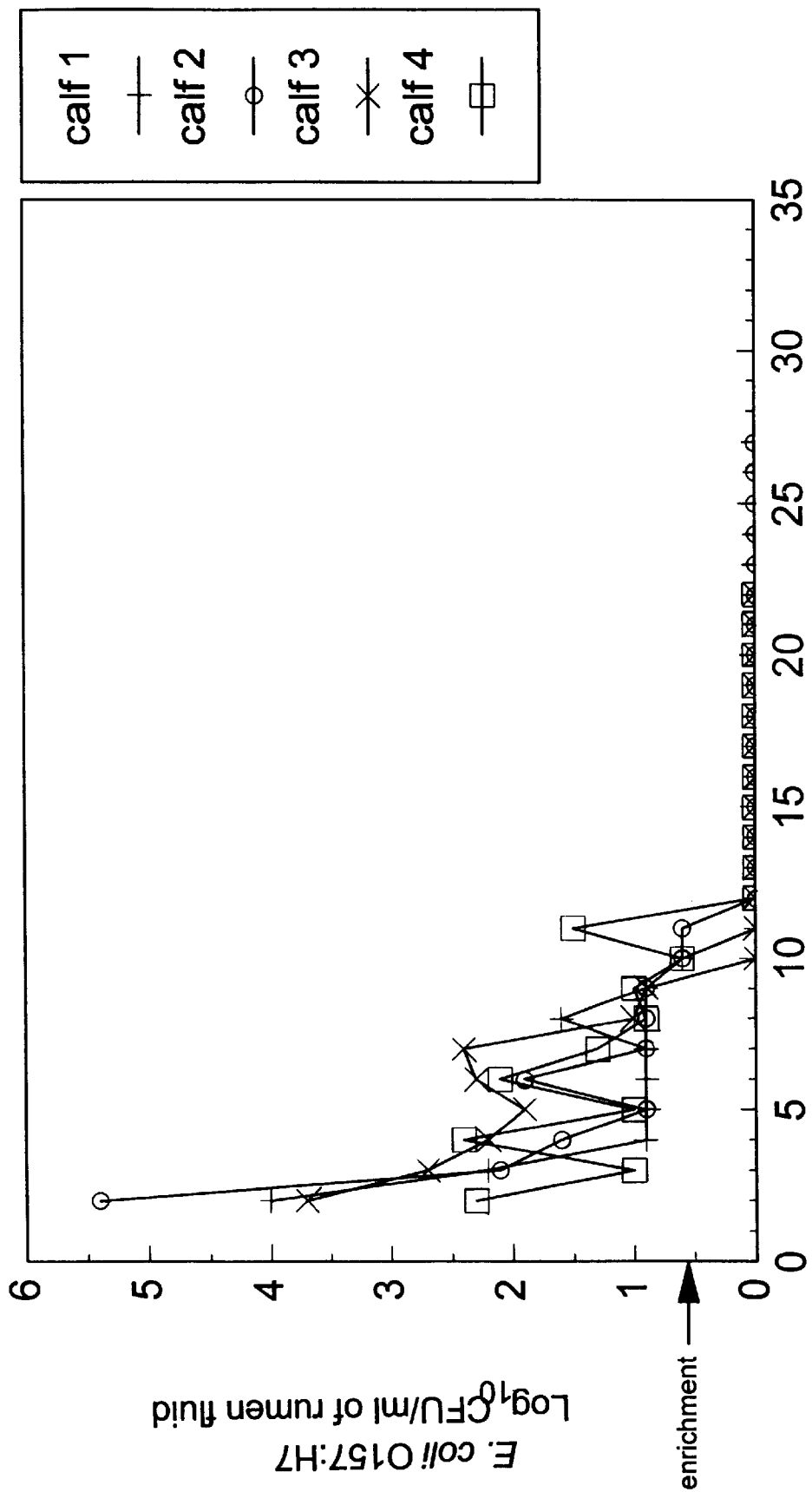
FIG. 7. is a graph of the fate of *E. coli* O157:H7 in rumen fluid of calves treated with dominant probiotic bacteria 1 to 3 days after administration of *E. coli* O157:H7. Arrow indicates detection of *E. coli* O157:H7 only by an enrichment procedure.
Figure 8:
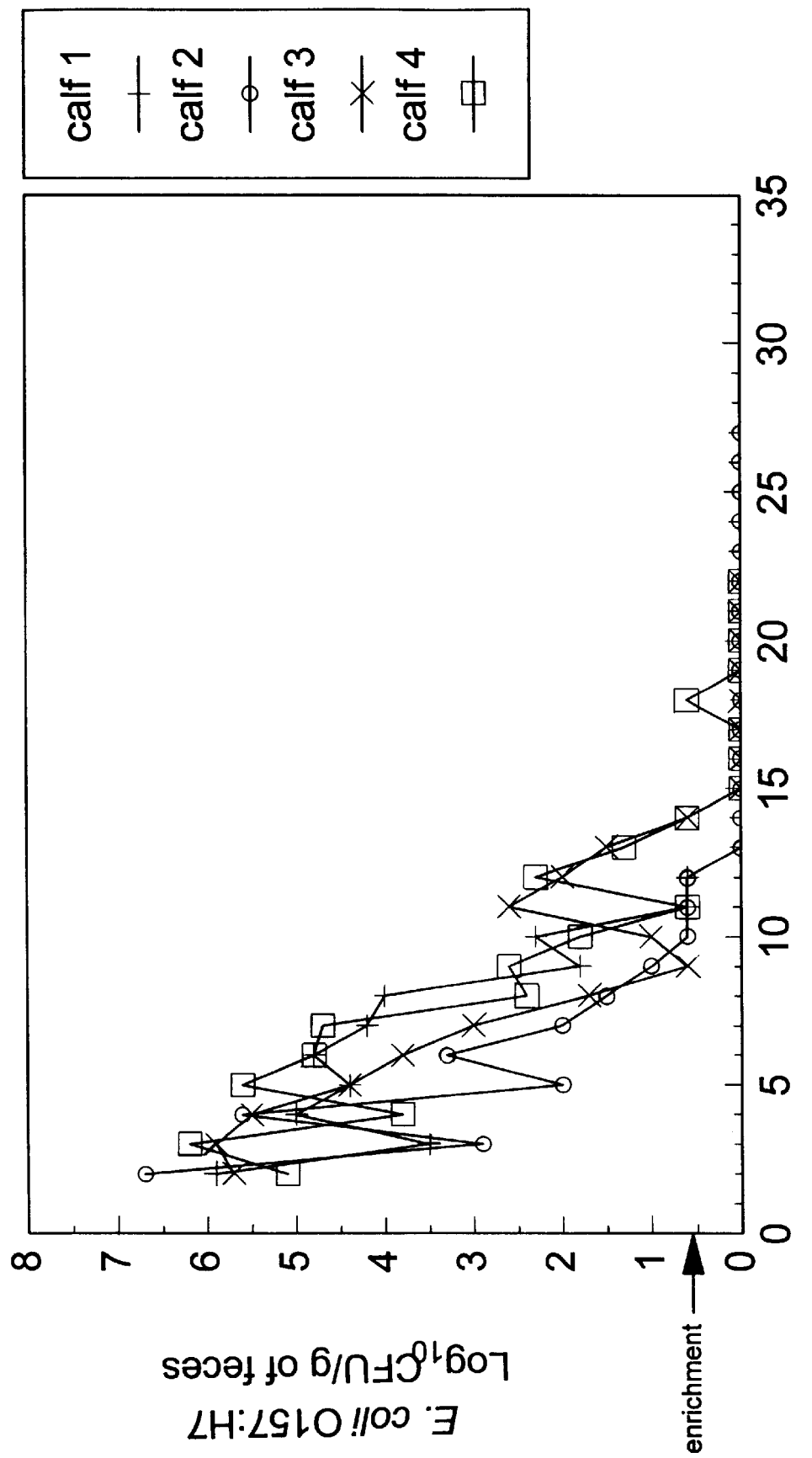
FIG. 8. is a graph of the fate of *E. coli* O157:H7 in feces of calves treated with dominant probiotic bacteria 1 to 3 days after administration of *E. coli* O157:H7. Arrow indicates detection of *E. coli* O157:H7 only by an enrichment procedure.

Four calves were treated with a mixture of four strains of probiotic bacteria (strains 271, 786, 797, and 1019) 1 to 3 days after administering E. coli O157:H7. E. coli O157:H7 was detected in rumen samples for up to 6 days in 1 animal, 8 days in two, and 9 days in one (FIG. 7). E. Coli O157:H7 was detected in feces for up to 10 days in two animals, 11 days in one, and 15 days in one (FIG. 8). At necropsy (two at 22 days and two at 27 days), E. coli O157:H7 was not recovered from samples of rumen or colon (tissue or contents) from any of these four animals. Only strains 271, 786, and 797 of probiotic bacteria were recovered from the four animals at the end of the study. Strain 1019 was not detected in any of the animals at the time of necropsy.

The foregoing examples illustrate the principles and practice of preventing and treating the carriage of E. coli O157:H7 by administering probiotic or dominant probiotic bacteria to an animal carrying E. coli O157:H7. Strains 271, 786 and 797 of E. coli were isolated and shown to be dominant probiotic bacteria. From the ease of isolation and number of strains obtained, it is evident that other dominant probiotic strains can be isolated and used to inoculate cattle or other animals for preventing or treating carriage of E. coli O157:H7. Different strains can be advantageous for different applications depending on animal species, breed, age, diet, living environment and management practices. All such bacterial strains isolated and/or used as generally described herein for effectively reducing or eliminating the amount of E. coli O157:H7 carried by an animal are within the scope of the invention. Methods of administration capable of providing an effective dose of probiotic or dominant probiotic bacteria to an animal include a variety of feeding, drinking, and other oral administration methods known to the art, using a variety of formulations containing the bacteria, all within the scope of the invention. All such variations and modifications, based upon or derived from the teachings and disclosures herein are deemed within the scope of the appended claims.

The following strains are deposited with the American Type Culture Collection, 10801 University Boulevard, Manassas, Va. 20110-2209, Aug. 13, 1997, pursuant to 37 CFR 1.801–1.809:

E. coli 271 ATCC Accession No. 202020
E. coli 786 ATCC Accession No. 202018
E. coli 797 ATCC Accession No. 202019

We claim:

1. A biologically pure culture having all of the identifying characteristics of a microorganism selected from the group of dominant probiotic bacteria consisting of E. coli 271, ATCC accession number 202020, E. coli 786, ATCC accession number 202018, and E. coli 797, ATCC accession number 202019.

2. A method for selecting dominant probiotic bacteria comprising the steps of:

isolating naturally-occurring bacterial strains from ruminant animal tissue fluids, digestive contents or feces, obtaining isolated strains;

culturing the isolated strains in liquid or solid media;

individually testing for the ability of each isolated strain to inhibit growth of E. coli O157:H7 in vitro, whereby strains having the ability to inhibit growth of E. coli O157:H7 in vitro are identified as a probiotic bacteria, subculturing the probiotic bacteria, and administering one or more strains of probiotic bacteria to a ruminant animal, and reisolating reisolatable probiotic bacteria from digestive contents or feces of said animal after a predetermined time, whereby the reisolatable probiotic bacteria are identified as dominant probiotic bacteria.

3. The method of claim 2 wherein the probiotic bacteria possess a selectable marker trait.

4. The method of claim 2 wherein the probiotic bacteria are distinguishable from one another by DNA restriction fragment digest patterns.

5. The method of claim 2 wherein the animal is a bovine.

6. A method for preventing or treating carriage of E. coli O157:H7 by a ruminant animal comprising administering an effective amount of one or more strains of dominant probiotic bacteria selected according to the method of claim 3 to the digestive tract of said animal.

7. The method of claim 6 wherein the dominant probiotic bacteria is selected from the group consisting of E. coli 271 ATCC 202020, E. coli 786 ATCC 202018 and E. coli 797 ATCC 202019.

8. The method of claim 6 wherein the dominant probiotic bacteria are administered in a series of doses combined with drinking water.

9. The method of claim 6 wherein the dominant probiotic bacteria are administered in a series of doses combined with feed.

10. The method of claim 6 wherein the animal is a bovine.

11. An inoculant composition comprising a carrier and one or more strains of dominant probiotic bacteria selected from the group consisting of E. coli 271 ATCC 202020, E. coli 786 ATCC 202018 and E. coli 797 ATCC 202019.

12. The composition of claim 11 wherein the carrier comprises water.

13. The composition of claim 11 wherein the carrier comprises a substance edible by cattle.

* * * * *

UNITED STATES PATENT AND TRADEMARK OFFICE
CERTIFICATE OF CORRECTION

PATENT NO. : 5,965,128

DATED : October 12, 1999

INVENTOR(S) : Doyle, et al.

It is certified that error appears in the above-identified patent and that said Letters Patent is hereby corrected as shown below:

<u>In the claims:</u>

In claim 6 at column 12, line 31, delete "3" and replace with --2--.

Signed and Sealed this

Thirteenth Day of June, 2000

Attest:

Q. TODD DICKINSON

Attesting Officer     *Director of Patents and Trademarks*